(12) United States Patent
Sahbaee Bagherzadeh et al.

(10) Patent No.: US 10,973,472 B2
(45) Date of Patent: Apr. 13, 2021

(54) ARTIFICIAL INTELLIGENCE-BASED MATERIAL DECOMPOSITION IN MEDICAL IMAGING

(71) Applicant: Siemens Healthcare GmbH, Erlangen (DE)

(72) Inventors: Pooyan Sahbaee Bagherzadeh, Mount Pleasant, SC (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 63 days.

(21) Appl. No.: 16/292,695

(22) Filed: Mar. 5, 2019

(65) Prior Publication Data

US 2020/0281543 A1    Sep. 10, 2020

(51) Int. Cl.
| | |
|---|---|
| *A61B 6/03* | (2006.01) |
| *A61B 6/00* | (2006.01) |
| *G06T 7/00* | (2017.01) |
| *G06T 11/00* | (2006.01) |
| *G16H 50/50* | (2018.01) |
| *G06T 5/00* | (2006.01) |

(52) U.S. Cl.
CPC ............ *A61B 6/032* (2013.01); *A61B 6/4241* (2013.01); *A61B 6/482* (2013.01); *A61B 6/484* (2013.01); *A61B 6/585* (2013.01); *G06T 7/0012* (2013.01); *G06T 11/005* (2013.01); *A61B 6/405* (2013.01); *A61B 6/5205* (2013.01); *G06T 5/002* (2013.01); *G06T 11/008* (2013.01); *G06T 2207/10081* (2013.01); *G06T 2207/30004* (2013.01); *G06T 2211/408* (2013.01); *G16H 50/50* (2018.01)

(58) Field of Classification Search
CPC . G06T 2207/10081; G06T 2207/20081; G06T 7/0012; G06T 2207/20084; G06T 2211/408; G06T 2211/424; G06T 11/005; G06T 11/006; G06T 11/00; G06T 11/008; G06T 2200/24; G06T 2207/20072; G06T 2207/20076; G06T 2207/20104; G06T 2207/30096; G06T 2207/30101
See application file for complete search history.

(56) References Cited

U.S. PATENT DOCUMENTS

| | | | |
|---|---|---|---|
| 2014/0133729 A1 | 5/2014 | Goshen | |
| 2015/0371378 A1 | 12/2015 | Schmidt et al. | |
| 2018/0144214 A1* | 5/2018 | Hsieh | G06N 3/08 |
| 2018/0144466 A1* | 5/2018 | Hsieh | G06T 7/0012 |

(Continued)

FOREIGN PATENT DOCUMENTS

CN          109242920 A          1/2019

OTHER PUBLICATIONS

U.S. Appl. No. 16/199,392, filed Nov. 26, 2018.

(Continued)

*Primary Examiner* — Golam Sorowar

(57) ABSTRACT

For material decomposition in medical imaging, a machine-learned model is trained to decompose. For example, spectral CT data for a plurality of locations is input, and the machine-learned model outputs the material composition. Using information from surrounding locations for the decomposition by the machine-learned model for a given location may allow for more accurate material decomposition and/or three or more material decomposition.

18 Claims, 2 Drawing Sheets

(56) References Cited

U.S. PATENT DOCUMENTS

| | | | | |
|---|---|---|---|---|
| 2018/0315188 A1* | 11/2018 | Tegzes | ................. | G06T 7/11 |
| 2019/0244348 A1* | 8/2019 | Buckler | ................. | G06T 7/11 |
| 2019/0261938 A1* | 8/2019 | Sevenster | ............. | G06T 7/0012 |
| 2020/0093451 A1* | 3/2020 | Nett | ................. | A61B 6/545 |
| 2020/0160509 A1* | 5/2020 | Pack | ................. | G06N 3/084 |
| 2020/0163637 A1* | 5/2020 | Choi | ................. | A61B 6/032 |
| 2020/0184278 A1* | 6/2020 | Zadeh | ................. | G06F 16/953 |
| 2020/0210767 A1* | 7/2020 | Do | ................. | G06N 3/08 |
| 2020/0237319 A1* | 7/2020 | Yi | ................. | G06T 11/005 |

OTHER PUBLICATIONS

Mendonça, Paulo RS, et al. "A flexible method for multi-material decomposition of dual-energy CT images." IEEE transactions on medical imaging 33.1 (2014): 99-116.

Symons, Rolf, et al. "Photon-counting CT for simultaneous imaging of multiple contrast agents in the abdomen: an in vivo study." Medical physics 44.10 (2017): 1-22.

Extended European Search Report received in corresponding EP Application No. 20161178.1, dated Aug. 11, 2020.

* cited by examiner

ARTIFICIAL INTELLIGENCE-BASED MATERIAL DECOMPOSITION IN MEDICAL IMAGING

BACKGROUND

The present embodiments relate to material decomposition in medical imaging. Spectral computed tomography (CT) decomposes measurements at different energies into different base materials using material decomposition techniques. For example, bone and contrast agent (e.g., iodine) are distinguished in a two-material decomposition. Existing material decomposition algorithms decompose for individual locations (e.g., voxels) based on the measurements for the individual locations. Beam hardening artifacts and statistical noise due to the tradeoff between limited photons in systems with a high number of energy bins and width of the energy bins in systems with low number of energy bins cause inaccuracies in decomposition.

Dual energy scans cannot separate more than two materials unless one of the materials has k-edge characteristics (i.e., measurement at more than two energy levels do not provide additional info). Three or more materials may be decomposed using additional bins or energy thresholds. The statistical noise level substantially increases for material decomposition for more than two materials, resulting in errors and inaccuracies. With more energy thresholds or energy bins for distinguishing between a larger number of materials, there are fewer photons in each energy bins since the total clinical dose is limited. As the energy bins are narrowed for more materials, there is more beam hardening.

SUMMARY

By way of introduction, the preferred embodiments described below include methods, systems, instructions, and non-transitory computer readable media for material decomposition in medical imaging. A machine-learned model is trained to decompose. For example, spectral CT data for a plurality of locations is input, and the machine-learned model outputs the material composition. Using information from surrounding locations for the decomposition by the machine-learned model for a given location may allow for more accurate material decomposition and/or three or more material decomposition.

In a first aspect, a method is provided for material decomposition in a medical imaging system. A patient is scanned with a spectral computed tomography (CT) system. The scanning provides spectral CT data representing the patient. A machine-learned model generates, in response to the spectral CT data, the material decomposition for each of a plurality of locations. An image of the material decomposition for the plurality of the locations is displayed.

In a second aspect, a system is provided for material decomposition. A medical scanner for scanning a patient is configured to output data representing an interior region of the patient. An image processor is configured to apply an artificial intelligence to decompose two or more materials represented by the data. A display is configured to display an image for at least one of the two or more materials.

In a third aspect, a method is provided for material decomposition in a medical imaging system. A patient is scanned with the medical imaging system, providing data representing the patient. A machine-learned model generates, in response to the data, the material decomposition for each of a plurality of locations based on the data for neighboring ones of the locations. The material decomposition is a three or more material decomposition. An image or images of the material decomposition for the plurality of the locations is displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Deep learning or other machine learning is used for multi-material decomposition in medical imaging. Being trained by thousands of images and decomposed images, such as from traditional two and/or three material decomposition algorithms, the machine-learned model is not limited to use the information only from the individual voxels to extract the decomposed information. Machine learning may train on labeled data with spatial information (e.g., planar and z axis) and/or temporal information (e.g., timing relative to contrast agent injection) for each location. Having access to the information over time and/or space may allow for more accurate classification of the pixel material and/or better estimation of the density of each material. Different material concentration and hence material-specific maps are provided in a way that has minimal impact from beam hardening artifacts and statistical noise.

Figure 1:
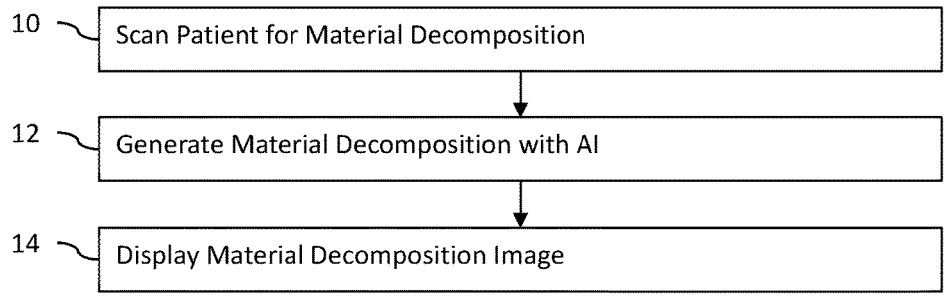
FIG. 1 is a flow chart diagram of one embodiment of a method for material decomposition in a medical imaging system.

FIG. 1 is a flow chart of one embodiment of a method for material decomposition in a medical imaging system. A machine-learned model is used in material decomposition. Since the machine-learned model is trained from images, spatial consideration is provided for decomposing the materials for each given location from measurements.

The medical imaging system performs the acts. A medical imager, such as a CT system, performs act 10. An image processor performs act 12. The image processor uses a display screen to perform act 14. In one embodiment, the system of FIG. 4 performs the acts. In other embodiments, different devices perform any one or more of the acts. In one example, the CT system performs all the acts. In yet another example, a workstation, computer, portable or handheld device (e.g., tablet or smart phone), server, or combinations thereof performs one or more of the acts.

The acts are performed in the order shown (e.g., top to bottom or numerical) or other orders. Additional, different, or fewer acts may be provided. For example, the method is performed without act 14. As another example, acts for configuring a medical scanner, such as for selecting the application and/or materials to be decomposed, are provided.

In act 10, a medical imaging system scans a patient. Any medical imaging system may be used. For example, a spectral CT system scans the patient. The spectral CT system includes an x-ray source or sources that may operate at different energies. Alternatively or additionally, a detector allows for detection at different energies, such as having multiple detectors or thresholds applied to detected x-ray photons. Dual energy or photon counting CT systems may be used. Using spectral CT, measurements reconstructed in Hounsfield or other density or attenuation values from different energies may be used to derive material composition.

The scan provides data representing an interior region of the patient. Spectral CT data is provided by a spectral CT system. Other data may be provided by a spectral CT or other medical imaging system. After reconstruction, the data represents a planar region of the patient. A volume may be represented, such as a stack of slices or planar regions.

The data is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format (i.e., scan or voxel data). As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for anatomical imaging, such as scan data representing spatial distribution of anatomy of the patient.

The data is obtained by scanning the patient. The scan data may be provided in or by the medical scanner, loaded from memory, and/or by transfer via a computer network. For example, previously acquired scan data is accessed from a memory or database. As another example, scan data is transmitted over a network after acquisition from scanning a patient.

Data different than the scan data may be acquired. For example, task-specific information is acquired. The task-specific information may be an identification of the region scanned (e.g., body region), existence of contrast agent in the scanned region, pathology information, scan settings (e.g., x-ray source energies, energy thresholds, photon count range, gantry position, range of movement, and/or reconstruction settings), and/or patient medical information. As another example, injection protocol information is acquired. The time of injection, the time of scan, the volume of contrast agent injected, the change in injection over time, the type of contrast agent, and/or other contrast agent information may be acquired.

In act 12, an image processor generates a material decomposition for one or more locations in the scanned region of the patient. The image processor determines the material composition for each of a plurality of locations, such as determining for each pixel or voxel location.

The material decomposition may be a classification, such as identifying whether a given material exists at the location. The classification may be two material, three material, or four or more materials. The material decomposition is for material labeling, identifying whether one of two or more materials is at the location. Alternatively or additionally, the material decomposition provides concentration, density, or relative amount (e.g., volume, attenuation, or density) of the different materials at each location. The concentration of each material for each location is determined.

Some example, two material decompositions may be of bone and iodine (e.g., contrast agent), blood and plaque, kidney soft tissue and kidney stone, lung tissue and lung vessel, gout (e.g., uric acid crystals) and blood, brain hemorrhage (e.g., marrow and bone), heart pulmonary blood volume (PBV)(e.g., fat and soft tissue) or bone marrow (e.g., cerebrospinal fluid and hemorrhaging tissue). Some example three material decompositions may be liver virtual non-contrast (VNC) (e.g., fat, soft tissue, and iodine), lung PBV (e.g., air, soft tissue, and iodine), or virtual unenhanced (air, water, and iodine). Three material decompositions may allow for use and distinguishing between tissue and two or more different types of contrast agents. Any type of materials may be used in decomposition of two or more materials in the patient.

The image processor generates the material composition with a machine-learned model. In response to input of data (e.g., the spectral CT data), the machine-learned model outputs the material decomposition for each of a plurality of locations. The input is by applying values of an input feature vector, such as values of the scan data, to the machine-learned model. For example, the spectral CT scan data for a patient is input. Features derived from the spectral CT data (e.g., Haar wavelets) may be input.

Other data than scan data may be input. The other data may include clinical data, biochemical measurements, genetic data, patient history, family history, or other patient data. The other data may be a scan characteristic and/or injection information. The scan characteristic may be any task specific information, such as scan settings and/or the application (e.g., lung material decomposition). The injection information may be any information from the injection protocol (e.g., timing, volume, and/or type of contrast agent) or other contrast agent information where contrast agents are used.

The scan characteristic and/or injection information is used to select a material or task-specific machine-learned model to apply and/or is used as input the machine-learned model. The machine-learned model may have been trained based on a database of past image acquisitions covering a wide range of scan phases (i.e., relative timing of the scan to contrast agent injection) and conditions (e.g., scan settings and/or task). For each available dataset in the training data, the task-specific information and information from the injection protocols, if any, may be combined with the actual acquired images to find a correlation between the values at a given location and time and concentration values for each material at the location. In other embodiments, scan characteristic and/or injection information is not used to select the model and/or as input to the model.

In one embodiment, the data from the scan is segmented. The segmentation isolates data representing a particular region (e.g., organ) in the patient. The segmented data is input. The segmentation may be used to identify the organ or region represented in the scan. This identification may be used as task-specific information for selecting the model and/or an input to the model. For example, the segmentation results or identification are used to identify or help identify the materials to be decomposed (e.g., heart verses lungs and corresponding materials).

The machine-learned model generates a material decomposition. By applying the values of the input vector, the output is generated. The machine-learned model is trained to generate the output in response to the input. Machine learning uses training data of labeled or ground truth material decomposition to learn to classify (e.g., material labeling) and/or to regress (e.g., concentrations of different materials). The training data is used as knowledge of past cases to train the model. The training associates the features of the input vector with material decomposition.

Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used.

In one embodiment, the classification and/or regression is by a machine-learned model learned with deep learning. Any deep learning approach or architecture may be used. For example, a convolutional neural network (CNN) is used. A supervised deep learning-based CNN may be trained on images with similar material and the Hounsfield (HU) values from individual voxels. Reconstructed CT images and decomposed material images as labeled voxels are used for training. As another example, the deep learning is based on a recurrent neural network (RNN) architecture. The RNN may include a long-short term memory architecture where the memory or memories are used for input data, features, and/or outputs for other locations and/or from other times relative to the injection of contrast agent. The spatial and/or temporal priori information is used to predict the decomposition of a location, which may reduce the impact of beam hardening and statistical noise. In contrast enhanced CT images with one or more contrast agents, RNN with the capability of using the time dependent information from each location may help predict the concentration of contrast agent in different organs. Other neural network architectures or networks may be used, such as an image-to-image, generative adversarial network, or U-net where scan data is input and a spatial representation is generated from deep learned features.

The neural network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided.

In another embodiment, sparse dictionary encoding is used for the machine learning. The machine-learned model is trained to provide a dictionary embedding. The signatures or other sparse encoding represented in the input data is learned for material decomposition, similar to word embedding (e.g., word2vec) trained from text data.

The machine-learned model, with or without deep learning, is trained to associate the ground truth (output material decomposition) to the extracted values of one or more features. Deep learning learns the features from the input data. Other types of machine learning may associate based on manually programmed or hand-coded input features. The machine-learning uses training data with ground truth to learn to estimate or classify based on the input vector. The resulting machine-learned model is an architecture with learned weights, kernels, connections, and/or other operations.

Figure 2:
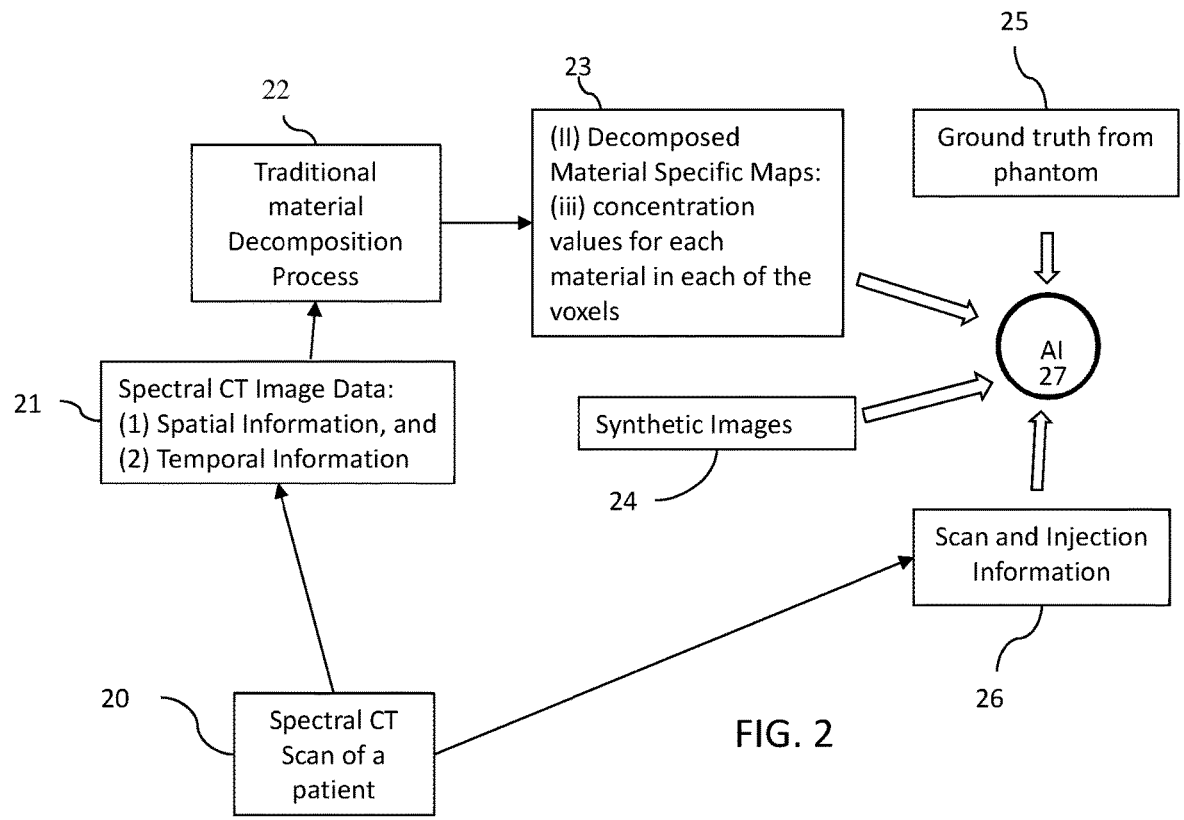
FIG. 2 illustrates training of an artificial intelligence for material decomposition.

FIG. 2 shows one embodiment for training with machine learning. The machine-learned model is an artificial intelligence (AI) 27 learned from training data. The training data includes samples from one or more sources, such as synthetically generated images 24, decomposed material maps 23 with material classification and/or concentration, and/or decomposed material maps 25 from one or more phantoms with different materials. Scan and/or injection information 26 may also be provided as an input (i.e., included for each training sample). The decomposed material maps 23 is from spectral CT scans 20 of many different patients where traditional material decomposition processes 22 are applied to the spectral CT data 21 including spatial and/or temporal distribution of measurements. The scan and/or injection information 26 is provided as part of the scan 20. To train, a large database of ground-truth labeled samples is acquired.

One of the major challenges or limitations in developing supervised deep learning models is the lack of enough annotated images for training due to the inherent difficulties of manual segmentation and labeling the contrast enhanced images. In one embodiment, the machine-learned model is trained using spectral CT-based material decomposition imaging as the ground truth. Spectral CT imaging is performed. The reconstructed scan data at the different energies are used as the input samples. Traditional two or three material decomposition software is applied. Previously validated 2-material and 3-material decomposition algorithms provide sufficient supervised labeled images. Any material decomposition-based applications, including iodine map, VNC, 3-material, etc. may be a reliable source of supervised training data, providing material labeling and/or concentration estimates as the ground truth.

In another embodiment, the machine-learned model is trained using CT-based material decomposition imaging of a phantom with known materials as ground truth. The training data contains images from scans of phantoms with inserts of different materials. The known materials provide the labels or ground truth for the images. The scan data used to form the images is used as the input samples. Using the phantom, the ground truth may be the known concentration of each material in each insert or the proportion of different materials in mixed inserts. The phantoms may be anthropomorphic or cylindrical. Vials with different known concentrations may be used.

In yet another embodiment, the machine-learned model is trained using synthesized CT model-based material decomposition imaging as ground truth. The scan region is modeled using known characteristics of different materials. Any physics or biomechanical model may be used. The model of the scan region may be repeated many different times with different spatial and/or temporal distributions of materials and/or concentrations. The modeling may be constrained by statistical analysis of samples from patients. A scanner simulation, such as DRASIM (Siemens), DukeSim (Duke), CatSim (GE), or computational anthropomorphic phantom (e.g., XCAT) is performed from each model of the scan region. The result is scan data simulated from the scan region model without actual scanning of the patient. The ground truth material labels and/or concentrations are known from the scan region model. The simulated scan data and material decomposition ground truth maps form the training data. The training data is simulated, providing synthetic data from modeling rather than from scanning patients or phantoms.

The training may use quality information. Training samples with better quality in the scan data and/or other input values and/or with better quality in the ground truth are weighted more heavily in the training than poor quality input and/or ground truth. The machine-learned model is trained with an image quality rating for training samples or ground truth. To account for image quality (e.g., image noise in the ground truth material decomposition maps), each ground truth image of material is augmented with the quantification of an "image quality" metric. Any image quality metric may be used, such as signal-to-noise ratio, level of artifact, or measure of beam hardening. The image quality rating may be computed algorithmically based on different image features (e.g., signal-to-noise ratio), annotated by a clinical team, or a combination of both. The training uses the rating in the optimization to minimize differences of the machine-learned model output from the ground truth. Where the rating is not used, the training optimizes the model to minimize differences of the estimated or classified output from the ground truth without rating-based weighting.

After the model is trained, the model is applied to previously unseen data. For a new patient, the scan data with or without other input information is applied to the machine-learned model. The machine-learned model outputs the material decomposition. The material decomposition is output for one or more locations. The material decomposition is output as a class membership (e.g., what material is at the location or material label) and/or a regression of concentration (e.g., amount of each material at the location).

Since the machine-learned model is trained on and uses as input a spatial and/or temporal distribution of measures from the patient, the output for a given location at a given time is informed by information from other times and/or locations. For example, the material decomposition for one location is based on scan data (e.g., spectral CT data) for that location and a plurality of neighboring locations. The window defining the neighboring locations may be of any size. The training data contains not only the scan data for individual voxels as the input but also for neighboring voxels in the reconstructed images and ground truth. Neighboring locations in the same plane and/or neighboring locations from other slices (e.g., planar neighbor voxels as well as z-axis (previous and next slices)) are used.

Alternatively or additionally, the output material decomposition from neighboring locations formed from the scan data is used for decomposing for a given location. In yet other embodiments, values for one or more features calculated for the other locations by or in the machine-learned model are used. The neighboring information (e.g., feature values or material decomposition) is priori information to predict the decomposition of a location (e.g., a voxel).

Using neighboring information may reduce the impact of beam hardening and/or statistical noise. In contrast enhanced CT images with one or more contrast agents, time dependent information from each voxel may help to predict the concentration of contrast agents in different organs.

The machine-learned model is applied for different locations. For each location, the scan data from surrounding locations and/or times relative to the injection protocol are used to classify or estimate. The machine-learned model is applied to different windows of scan data to decompose the materials for different locations. Alternatively, the scan data is input for multiple locations, and the machine-learned model outputs material decomposition for the multiple locations.

In act 14 of FIG. 1, the image processor generates and a display displays an image of the material decomposition for the plurality of the locations. The material decomposition image may be visualized on the CT or medical scanner or on another device, such as an imaging workstation.

Figure 3:
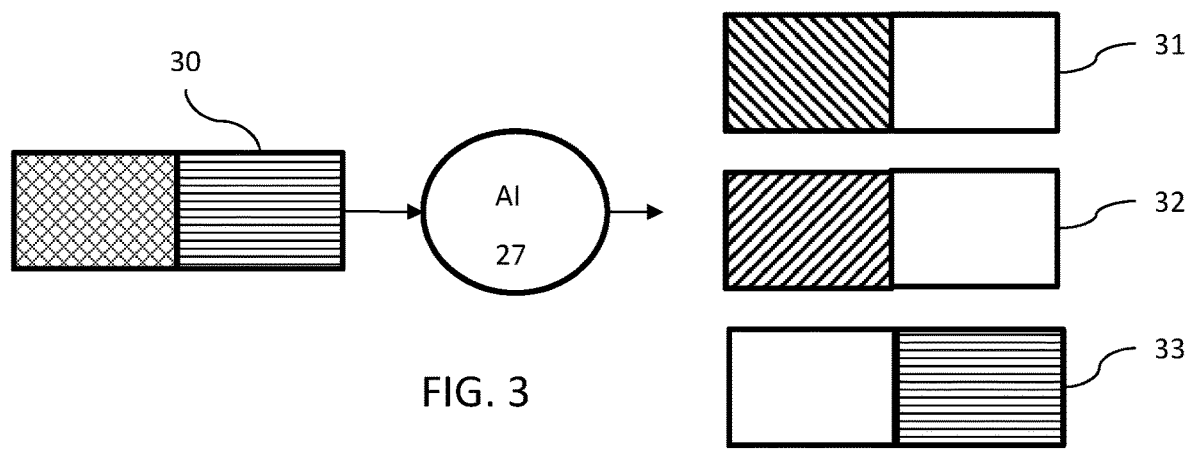
FIG. 3 shows images of concentration of different materials from material decomposition.

The image is of one material. For example, a distribution of locations labeled for the material is displayed. Images for distribution of other materials may be displayed. Material maps for the different materials are generated as images and displayed. FIG. 3 shows an example where the scan data is shown as a reconstructed grayscale image 30. The AI 27 outputs material decomposition used for three images 31, 32, 33, where one image is provided for each of two materials (iodine image 31; gadolinium image 32) and a virtual non-contrast image 33. The images 31, 32, 33 may be for three different materials. Alternatively, different materials modulate different aspects of a same image, such as using different colors for different materials. The one image shows spatial distributions of the different materials, such as spatial distribution of two different contrast agents with or without bone. Any material decomposition imaging may be used.

Images showing material composition at different times relative to an injection initiation may be generated and displayed. A video of material decomposition as a function of time may be provided. The variation over time of material decomposition for a single location or line of locations may be displayed as a graph or graphs.

Quantities may be calculated from the material decompositions, such as an area or volume. The quantities may be displayed with or separately from the images. The material decomposition image or images may be overlaid on or displayed adjacently to a CT image of the patient tissue without material decomposition.

The material decomposition and/or images generated from the material decomposition may be transmitted to the display (e.g., a monitor, workstation, printer, handheld, or computer). Alternatively or additionally, the transmission is to a memory, such as a database of patient records, or to a network, such as a computer network.

In one embodiment, the machine-learned model is used for part of material decomposition, and spectral CT (i.e., traditional or algorithm-based) material decomposition is used for another part of the material decomposition. Both may be used independently. The resulting decompositions are displayed adjacent to each other for comparison. Alternatively, the results are averaged or combined to form the decomposition image or images. Both approaches may be used in a hybrid. For example, the algorithm-based material decomposition is applied. The machine-learned model is trained to refine the material decomposition from the algorithm-based material decomposition results with or without input of other data (e.g., scan data). In any of these or other combinations, the resulting images are a function of output of the spectral CT material decomposition and the machine-learned model.

Figure 4:
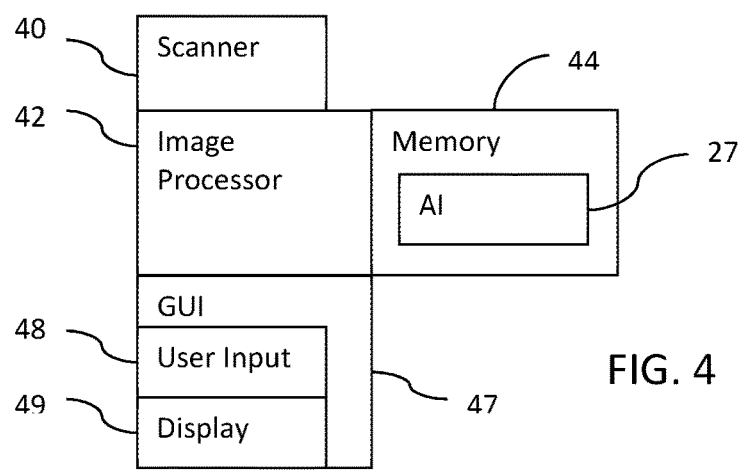
FIG. 4 is one embodiment of a system for material decomposition.

FIG. 4 shows a system for material decomposition. The system implements the method of FIG. 1 or another method to output material composition for an interior region of a patient, such as shown in FIG. 3. An AI 27 is used to perform material decomposition from data for a patient.

The system includes a medical scanner 40, an image processor 42, a memory 44, a graphical user interface (GUI) 47 with a user input 48 and a display 49, and one or more machine-learned models as the AI 27. Additional, different, or fewer components may be provided. For example, a network or network connection is provided, such as for networking with a medical imaging network or data archival system or networking between the scanner 40 and the image processor 42. In another example, the user input 48 is not provided. As another example, a server is provided for implementing the image processor 42 and/or AI 27 remotely from the scanner 40.

The image processor 42, memory 44, user input 48, display 49, and/or AI 27 are part of the medical scanner 40. Alternatively, the image processor 42, memory 44, user input 48, display 49, and/or AI 27 are part of an archival and/or image processing system, such as associated with a medical records database workstation or server, separate from the CT scanner 40. In other embodiments, the image processor 42, memory 44, user input 48, display 49, and/or AI 27 are a personal computer, such as desktop or laptop, a workstation, a server, a network, or combinations thereof.

The medical scanner 40 is a medical diagnostic imaging scanner for material decomposition. For example, the medical scanner 40 is a spectral CT scanner operable to transmit and/or detect radiation at different energies. A gantry supports a source or sources of x-rays and supports a detector or detectors on opposite sides of a patient examination space from the source or sources. The gantry moves the source(s) and detector(s) about the patient to perform a CT scan. Various x-ray projections are acquired by the detector from different positions relative to the patient. Computed tomography solves for the two or three-dimensional distribution of the response from the projections, reconstructing the scan data into a spatial distribution of density or attenuation of the patient.

The medical scanner 40 is configured by an application and/or settings to output data representing an interior region of the patient. The medical scanner 40 scans the patient. After reconstruction (e.g., computed tomography or Fourier transform), scan data representing different locations in the patient is provided by the medical scanner 40. By scanning at different times or in an on-going manner, scan data representing the patient at different times may be generated.

The memory 44 may be a graphics processing memory, a video random access memory, a random-access memory, system memory, cache memory, hard drive, optical media, magnetic media, flash drive, buffer, database, combinations thereof, or other now known or later developed memory device for storing data. The memory 44 is part of the medical scanner 40, part of a computer associated with the image processor 42, part of a database, part of another system, a picture archival memory, or a standalone device.

The memory 44 stores patient data, such as scan data, scan characteristics (e.g., settings or other task-specific information), and/or injection information. Any of the patient data discussed herein may be stored, such as values for features in the machine-learned model, material decompositions, and/or images. Training data may be stored. Model parameters or values for generating the training data may be stored. The memory 44 alternatively or additionally stores weights, connections, filter kernels, and/or other information embodying one or more machine-learned models (e.g., the AI 27). The memory 44 may alternatively or additionally store data during processing, such as storing information discussed herein or links thereto.

The memory 44 or other memory is alternatively or additionally a non-transitory computer readable storage medium storing data representing instructions executable by the programmed image processor 42 or a processor implementing the AI 27. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 42 is a general processor, central processing unit, control processor, graphics processor, digital signal processor, three-dimensional rendering processor, application specific integrated circuit, field programmable gate array, artificial intelligence processor, digital circuit, analog circuit, combinations thereof, or other now known or later developed device for applying the AI 27 to scan data and generating a classification or estimation of material composition. The image processor 42 is a single device or multiple devices operating in serial, parallel, or separately. The image processor 42 may be a main processor of a computer, such as a laptop or desktop computer, or may be a processor for handling some tasks in a larger system, such as in the medical scanner 40. The image processor 42 is configured by instructions, design, hardware, and/or software to perform the acts discussed herein.

The image processor 42 is configured to apply the AI 27 to decompose scan data to two or more materials represented by the scan data. The AI 27 uses the data from neighboring ones of the locations in the decomposition to find the two or more materials for each of the locations. The AI 27 was trained to decompose for two, three, or more materials. The materials may depend on the application or medical pathology of interest. The AI 27 for that pathology or application may be selected and used to decompose for the appropriate or task-specific materials.

The AI 27 uses learned knowledge to decompose. The AI 27 is machine-learned model, such as a machine-learned neural network, and was trained from synthetically generated material decomposition using a model of the medical scanner, scanning a phantom of known materials, or both the synthetically generated material decomposing using the model and scanning the phantom. The training data may additionally or alternatively be from an algorithm for material decomposition used in medical imaging.

The image processor 42 is configured to apply the input feature vector to the AI 27. The image processor 42 may be configured to calculate values for features and input the values to the AI 27 or use the values as part of the AI 27. The AI 27 is implemented by the image processor 42 or other processor with access to the definition or learned parameters defining the AI 27 stored in the memory 44 or other memory.

The image processor 42, using the AI 27, is configured to output a material decomposition for one or more locations. For example, different combinations of the input data corresponding to different windows of locations are used to determine the material decomposition for each of the sample or scan locations, voxel locations, pixel locations, or locations in a region of interest. The image processor 42 is configured to generate one or more images of material composition.

The image processor 42 may be configured to generate a graphic user interface (GUI) 88 for input of values or data and/or for material decomposition images. The GUI 47 includes one or both of the user input 48 and the display 49. The GUI 47 provides for user interaction with the image processor 42, medical scanner 40, and/or AI 27. The interaction is for inputting information (e.g., selecting patient files) and/or for reviewing output information (e.g., viewing material decomposition images). The GUI 47 is configured (e.g., by loading an image into a display plane memory) to display the material decomposition images.

The user input device 85 is a keyboard, mouse, trackball, touch pad, buttons, sliders, combinations thereof, or other input device. The user input 48 may be a touch screen of the display 49. User interaction is received by the user input device 85, such as a designation of a region of tissue (e.g., a click or click and drag to place a region of interest). Other user interaction may be received, such as for activating the material decomposition.

The display 49 is a monitor, LCD, projector, plasma display, CRT, printer, or other now known or later developed devise for outputting visual information. The display 49 receives images of one or more materials from the material decomposition. The material decomposition images are displayed on the display 49. Graphics, text, quantities, spatial distribution of anatomy or function, or other information from the image processor 42, memory 44, CT scanner 40, or machine-learned classifiers 90 may be displayed.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for material decomposition in a medical imaging system, the method comprising:
    scanning a patient with a spectral computed tomography (CT) system, the scanning providing spectral CT data representing the patient;
    generating, by a machine-learned model in response to the spectral CT data, the material decomposition for each of a plurality of locations, where the material decomposition for each of the plurality of the locations is based on the spectral CT data for the location and a plurality of neighboring ones of the locations, where, for each location, the neighboring ones of the locations being locations within a window in space and/or time where the location is also within the window, the window defining the location and the neighboring ones used to generate the material decomposition of the location;
    transmitting the material decomposition for the plurality of the locations.

2. The method of claim 1 wherein scanning comprises scanning with the spectral CT system using dual energy or photon counting.

3. The method of claim 1 wherein generating comprises generating with the machine-learned model having been trained using CT-based material decomposition imaging as ground truth.

4. The method of claim 3 wherein generating comprises generating with the machine-learned model having been trained using CT-based material decomposition imaging of a phantom with known materials as ground truth.

5. The method of claim 1 wherein generating comprises generating with the machine-learned model having been trained using synthesized CT model-based material decomposition imaging as ground truth.

6. The method of claim 1 wherein generating comprises generating by the machine-learned model in response to the spectral CT data, scan characteristic, and injection information.

7. The method of claim 1 wherein generating comprises generating by the machine-learned model having been trained with an image quality rating for training samples.

8. The method of claim 1 wherein generating comprises generating with the machine-learned model comprising a convolutional neural network.

9. The method of claim 1 wherein generating comprises generating with the machine-learned model comprising a recurrent neural network having a long-short term memory.

10. The method of claim 1 wherein generating comprises generating by the machine-learned model having been trained with a dictionary embedding.

11. The method of claim 1 further comprising performing spectral CT material decomposition imaging, wherein the material decomposition is a function of output of the spectral CT material decomposition and the machine-learned model.

12. The method of claim 1 wherein generating comprises generating the material decomposition as a decomposition of three or more materials.

13. The method of claim 12 wherein generating comprises generating concentrations at each of the locations for the three or more materials, and wherein transmitting comprises displaying an image as a first material map for one of the three or more materials and displaying second and third material maps as other images for others of the three or more materials.

14. A system for material decomposition, the system comprising:
    a computed tomography scanner for scanning a patient, the scanner configured to output data representing an interior region of the patient, wherein the data represents a plurality of locations of the interior region;
    an image processor configured to apply an artificial intelligence to decompose two or more materials represented by the data, wherein the artificial intelligence uses the data from neighboring ones of the locations in the decomposition of the two or more materials for each of the locations, wherein the data from the neighboring ones comprises priori information from the neighboring ones of the locations; and
    a display configured to display an image for at least one of the two or more materials.

15. The system of claim 14 wherein the computed tomography scanner comprises a spectral computed tomography scanner.

16. The system of claim 14 wherein the artificial intelligence was trained to decompose the two or more materials as at least three materials.

17. The system of claim 14 wherein the artificial intelligence comprises a machine-learned neural network having been trained from synthetically generated material decomposition using a model of the medical scanner.

18. A method for material decomposition in a computed tomography imaging system, the method comprising:
    scanning a patient with the computed tomography imaging system, the scanning providing data representing the patient;
    generating, by a machine-learned model in response to the data, the material decomposition for each of a plurality of locations based on the data for neighboring ones of the locations, the material decomposition comprising a three or more material decomposition, the neighboring ones of the locations being part of a spatial and/or temporal distribution representing the patient where the neighboring ones of the locations are locations within the distribution with the location for which the material decomposition of the location is generated;

displaying an image or images of the material decomposition for the plurality of the locations.

* * * * *